Figure 1:
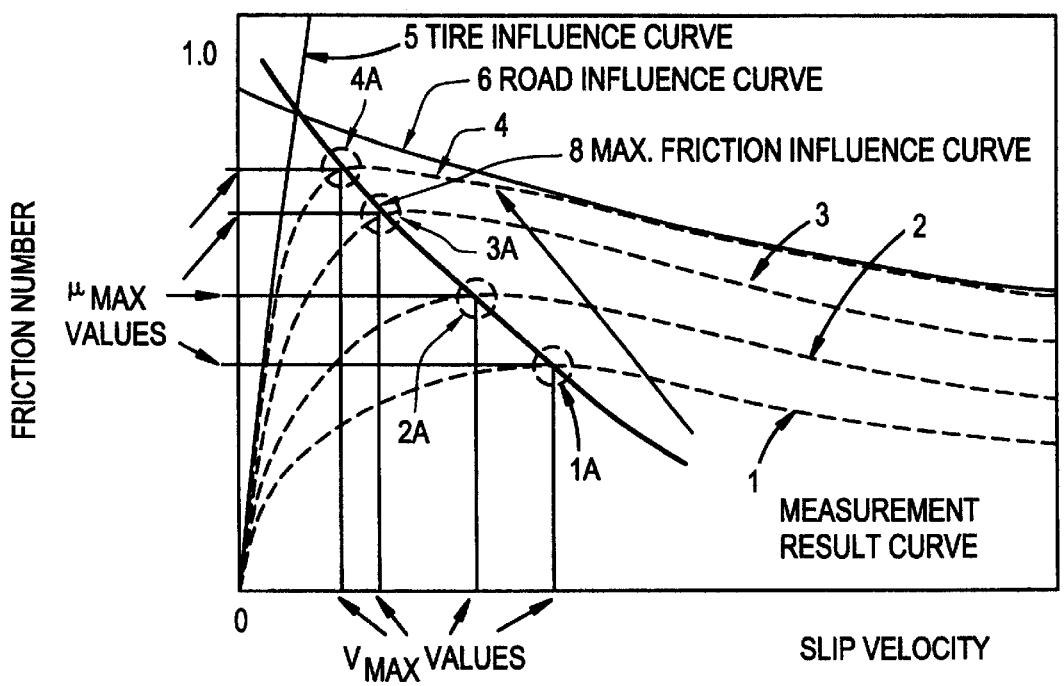

United States Patent
Andresen et al.

[19]

[11] Patent Number: 5,814,718
[45] Date of Patent: Sep. 29, 1998

[54] METHOD AND APPARATUS FOR MEASURING OR CONTROLLING FRICTION

[75] Inventors: Arild Andresen, Oslo; Oddvard Johnsen, Lier, both of Norway; Zoltan Rado, Györ, Hungary

[73] Assignee: Norsemeter A/S, Rud, Norway

[21] Appl. No.: 836,601

[22] PCT Filed: Nov. 3, 1995

[86] PCT No.: PCT/NO95/00206

§ 371 Date: May 2, 1997

§ 102(e) Date: May 2, 1997

[87] PCT Pub. No.: WO96/14564

PCT Pub. Date: May 17, 1996

[30] Foreign Application Priority Data

Nov. 4, 1994 [NO] Norway .................................. 944227

[51] Int. Cl.$^6$ .................................................. G01N 19/02
[52] U.S. Cl. .................................................................. 73/9
[58] Field of Search ........................... 73/9, 146; 303/139, 303/141–143; 701/82–91

[56] References Cited

U.S. PATENT DOCUMENTS 5,281,008  1/1994  Kawamura et al. .
5,311,433  5/1994  Igata et al. .

FOREIGN PATENT DOCUMENTS 0287862  10/1988  European Pat. Off. .
0444772  9/1991   European Pat. Off. .
3735673  5/1989   Germany .
4435448  4/1995   Germany .

*Primary Examiner*—Robert Raevis
*Attorney, Agent, or Firm*—Rothwell, Figg, Ernst & Kurz, P.C.

[57] ABSTRACT

The friction between vehicle wheels provided with rubber tires follows three influence curves (5, 6, 8). The friction between a wheel with rubber tire and a road surface is represented by a measuring result curve (1–4) the shape of which is determined symptotically from the rubber tire influence curve (6). Thus the measuring result curve (1–4) will have a characteristic shape with maximum values (1A–4A). The maximum friction is determined by the influence curve of the rubber tire and the road surface respectively, also denoted the maximum friction influence curve (8). Each influence curve has its mathematical model. In the mathematical model for the maximum friction influence curve (8) there is incorporated a slip speed, properties of the car tire and road surface-to-car tire properties. The car tire properties and the pavement-to-car tire properties can be determined as process parameters by measurement. Then the maximum friction will be a dependent variable of the slip speed alone, as long as the properties of the car tire and the road surface-to-car tire properties are unaltered. The invention can be utilized for measuring car tires or road surfaces and for controlling traction, i.e. braking or propulsions.

15 Claims, 2 Drawing Sheets

METHOD AND APPARATUS FOR MEASURING OR CONTROLLING FRICTION

This invention relates to a method for measuring or controlling friction relationships by interaction between a pneumatic vehicle rubber tyre and a surface during rolling movement with slip conditions between the wheel and the surface, comprising reel-time calculation of friction relationships by means of friction-slip speed relations during an acceleration or deceleration time interval for the rolling motion of the wheel relative to the surface.

The invention also comprises apparatus or equipment for use in the method for various applications that can utilize the fundamental solutions forming the basis of the invention.

At one hand, there is here the question of measurement, either of a vehicle rubber tyre or of a surface, such as a road or a runway at airports. On the other side, the invention can be utilized in controlling a traction process, i.e. either a braking effect or a propulsion effect for a vehicle,-including both automobiles and airplanes being provided with pneumatic rubber tyres. As far as airplanes is concerned, there will normally only be the question of controlling the braking effect. Control of the type discussed here, as a rule takes place during a rather short time interval, for example from fractions of a second to a few seconds. It is well known that in particular in the case of braking an optimal control of the short interval braking process will be of critical significance in many situations.

Measurement of the friction or traction properties of rubber tyres or wheels is of course also a very important field of use, such as for car tyre producers. On the other hand measurement of friction properties of runway or road surfaces is very significant to road builders, not the least when the road surface or runway has a coating or contamination, including ice or snow, which can influence the friction relationships.

For a long time, research has been made of the very complicated physical relationships and factors being of relevance within the technical field concerned herein, and the development in recent time in such respects can be considered to be represented, inter alia, by Norwegian Patent No. 165.856 and the corresponding U.S. Pat. Nos. 4,958,512 and 5,249,851. Moreover reference is made here to the applicants own publication "An Update on Road Grip Friction", distributed during IX PIARC Winter Road Congress, Seefeld, March 1994. Among other things, the publication contains a long list of references.

In European patent specification EP-287862 there is described applications of indirect and approximate methods for calculating friction between a pneumatic wheel and a road surface, based on measurements of vehicle velocity, rotational speed of the wheel and big changes of slip speed (vehicle velocity minus peripheral speed of the wheel) when the torque of a drive motor and thereby of the drive wheel is continuosly estimated-by-measuring supplied fuel. There is no attempt, however, at determining the friction relationship mathematically for further utilization for the purpose of control. Rather there is employed a trial-and-error method in order to identify the indirect influence of the maximum friction on the rotational speed of the wheel, and control based on the measured manipulated variable parameters for fuel among other things, being present just before the big change of slip speed took place.

This invention provides solutions based on new understanding gained by the inventors, including important mathematical relations for describing friction relationships which previously to a substantial degree have been studied empirically and with graphic methods after comprehensive measurements. Previously known methods in this field have been based on the observation of friction relationships as a function of percentage slip-or sliding between the peripheral surface of the wheel and the pavement. This type of observation in particular forms the basis of the patents referred to above. In contrast, it has been found in connection with the present invention, that it is highly advantageous to let the analysis and thus solutions be based on a measurement or calculation of the actual slip speed, i.e. the absolute relative velocity of movement between the wheel contact area and the interaction road surface. The magnitude of this slip speed has been found to be essentially relevant for the variations in friction relationships, for example during an emergency braking process.

The novel and specific features according to the invention in various applications thereof, are stated more closely in the claims.

The invention involves a number of advantages, comprising high accuracy and quickness both in measurements and for traction control. With the invention it has been made possible for the first time to provide a total or integrated and measureable representation of the friction relationships in connection with interaction between a pneumatic vehicle rubber tyre and a surface.

Figure 2A:
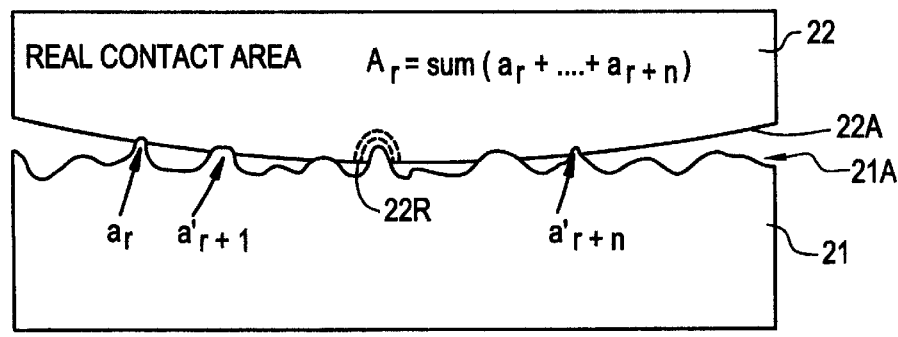
Figure 2B:
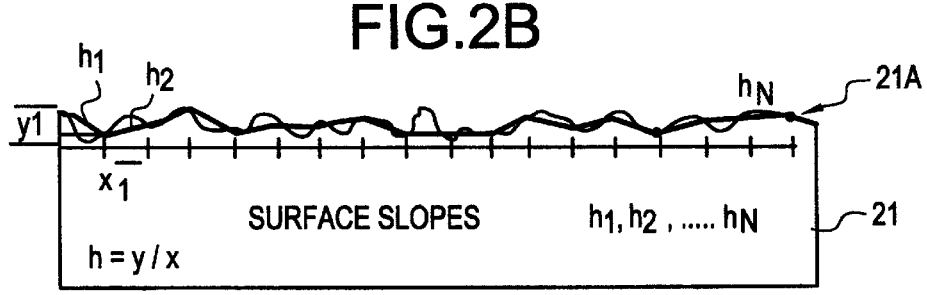
Figure 3:
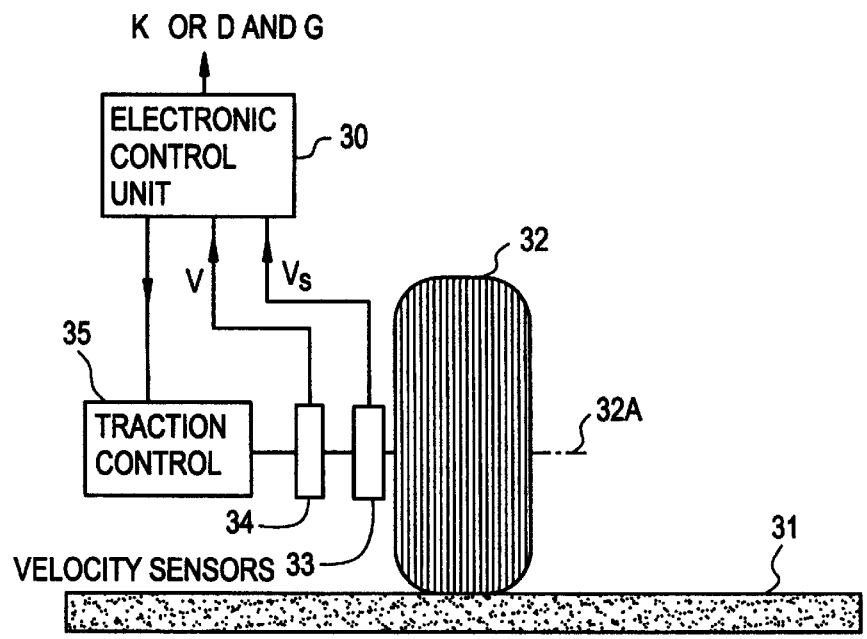
Figure 4:
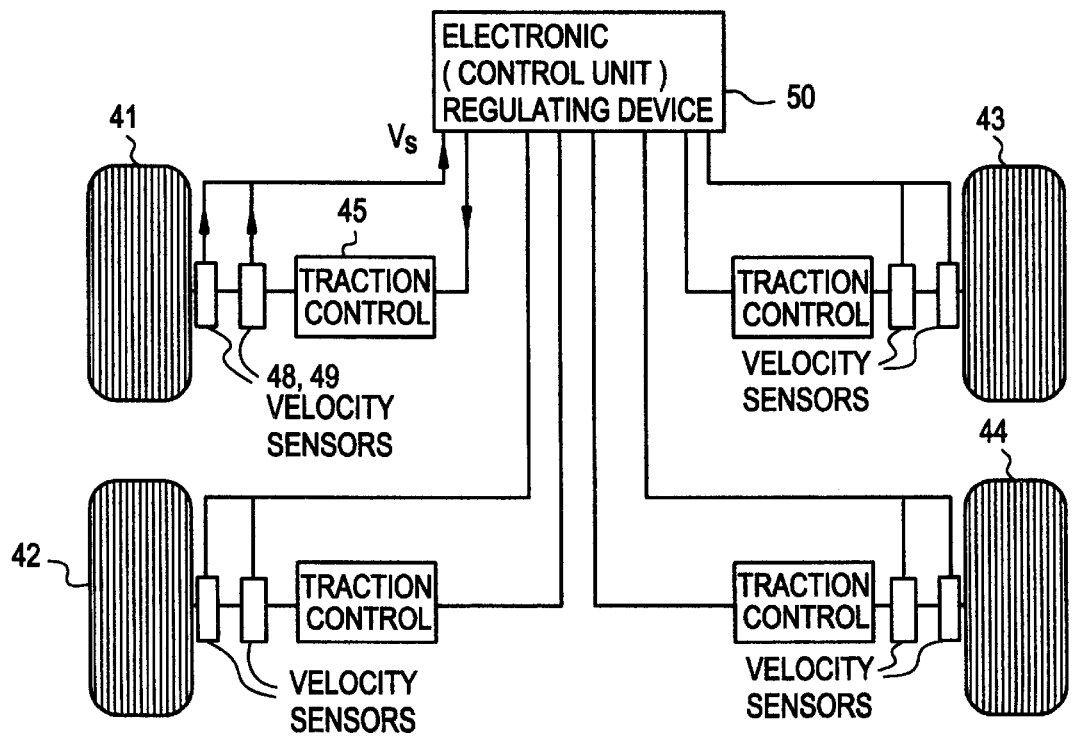

In the following description the invention will be explained more closely, with reference to the figures of drawings, in which:

FIG. 1 shows a diagram with curves relating to friction relationships as a function of slip speed, FIGS. 2A and 2B are highly enlarged crossed section through a road or runway and a portion of a wheel rolling thereon, for illustrating texture and dimension relationships of much significance in the present context, FIG. 3 in a simplified and schematic manner shows an arrangement for measuring friction relationships in order to determine traction properties of a rubber wheel and friction properties of a road surface respectively, and FIG. 4 in a correspondingly simplified and schematic manner shows an arrangement for controlling traction relationships or effects in connection with a vehicle. In the diagram of FIG. 1, there is shown curves being fundamental to the relationships discussed here. Curves 1 2, 3 and 4 can be considered to represent measurement results relating to friction as a function of slip speed, and these curves have a characteristic shape being in principle similar to corresponding curves measured as a function of percent slip, as for example according to the Norwegian Patent Specification mentioned above. It is in particular to be noted that such measurement curves typically have a maximum point or peak which in FIG. 1 is shown at 1A, 2A, 3A and 4A respectively, for the various curves 1, 2, 3 and 4.

The steeply rising curve portion at low slip speeds can be considered to approximate or to be confined by an asymptotic line 5 and in a corresponding manner the curve portions to the right hand side of the maximum points 1A, 2A, 3A and 4A have a relatively regular or similar course which can be considered to be confined by another asymptotic line 6. The inclination or slope of the initial portion represented by line 5, is mainly determined by the properties of the rubber wheel, whereas the curve portions for higher slip speeds, represented by line 6, are mainly determined by the surface, i.e. the friction properties of the runway or road surface.

As already indicated above, there has not previously been available methods for mathematically describing the shape of measurement curves of the type being represented by curves 1, 2, 3 and 4 in FIG. 1. In connection with this invention, it has been possible to find a mathematical model or relation which to a very good approximation describes this type of curve, namely:

$$\mu(V_S) = \mu_{max} \cdot e^{-\left(\frac{\ln\left(\frac{V_S}{V_{max}}\right)}{C}\right)^2} \quad (1)$$

In this relation (1) $\mu_{max}$ is the maximum value of a measurement curve as for example curves 1–4 in FIG. 1, and $V_{max}$ is the corresponding slip speed, which can also be denoted critical slip speed. $\hat{C}$ is a parameter representing macro texture and is closely related to the so-called "speed number" according to the known PIARC-model and the percent normalized gradient, ("PNG") as in the known PennState model. Thus both these models only consider the road surface aspect of the friction process between a pneumatic wheel and the road, for the purpose of expressing macro texture properties of the road surface and mainly the significance of macro structure for reducing the friction being experienced at increasing vehicle velocity. This relationship has formed the basis for monitoring the development of road surface macro texture over time (some years) as a factor in planning the maintenance of the road. The association to macro texture has been made to the negative inverse magnitude of the rise angle (the derivate) of the models when they have been converted to logarithmic form and has been found by observations by, inter alia, M. C. Lew and J. J. Henry, as described in "Prediction of Skid Resistance as a Function of Speed from Pavement Texture", Transportation Research Record 666 (1978, pp. 7–13. The PIARC model is described in "International PIARC Experiment to Compare and Harmonize Texture and Skid Resistance Measurements", AIPCR—Jan. 4, 1995. In connection with this invention it has been found that the ability of these models to express macro texture is improved by means of the logarithmic model (1) referred to, as this also comprises lower slip speed ranges when the pneumatic wheel is rolling at the very beginning of a braking or skidding procedure. Thus the position of $\mu_{max}$ can indicate the region where the PIARC and PennState models are no longer valid in the direction towards lower slip speeds. The PIARC model and the PennState model do not comprise-the determination of maximum friction, which is a significant improvement according to the logarithmic model (1) provided herewith. $\hat{C}$ is denoted shape factor by the inventors, since in view of its mathematical context it strongly influences and gives an adequate expression of the characteristic arcuate geometrical shape assumed by the friction measurement curves 1–4 in FIG. 1.

The model or relation (1) provided here is rather fundamental in the present connection and is based on physical observations of the gradient of the friction-slip speed ratio. The model forms a basis for much of what follows in this description, and can be considered to constitute an integral part of the following discussion.

Since the model describes the maximum point or peak and the critical slip speed (the position of the peak of the curve along the slip speed axis) it is able to describe the lowering of the maximum values and the displacment of the peaks with increasing vehicle velocity. The description of these phenomena leads to very important information on the micro and macro texture of the road surface as well-as the capability of the rubber wheel. The complete mathematical deductions in this connection and detailed analysis of texture or surface profile would lead to far in this description.

As will appear the relation (1) is a model with three parameters being considered to be independent of slip speed and vehicle velocity, the latter being the model variables. The three parameters of $\mu_{max}$, $V_{max}$ and $\hat{C}$. Other parameters can be derived from these, as will also be seen from the following analysis, but as the other parameters are functions of the above three parameters, they are not to be considered as model parameters even though they may have important physical significances.

Relation (1) will not in the following description be discussed more thoroughly, but under certain conditions and circumstances may be involved in some embodiments of the inventions.

It is important to be aware of the fact that corresponding values of $\mu_{max}$ and $V_{max}$ included in relation (1) can be determined by means of a mesurement method being described in Norwegian Patent 165.856 referred to above, for a given vehicle wheel and pavement or road surface. The maximum friction value $\mu_{max}$ is representative of the total or combined friction properties by interaction between the surface and the rubber wheel or tire, comprising the so called "real contact area", the relaxation spectra of the rubber tyre, the composition of the structure or texture and the density of surface grip points between the wheel surface and so forth. These notions will be explained more closely below with reference, inter alia, to FIG. 2.

As a certain, but moderate approach to the problems and the complicated relationships occuring by interaction between a rubber wheel and a surface on which the wheel rolls, in particular when taking into account a certain degree of slip or sliding during such rolling, reference is made to FIG. 2, which is subdivided in FIGS. 2A and 2B. In these figs. or drawings there is shown a highly enlarged cross section of a portion of a road surface 21 the surface profile or texture of which is denoted 21A. In the enlargement concerned it is clearly visible that the surface is rather rough or uneven, i.e. having a number of depressions and peaks of varying shapes.

In FIG. 2A there is also shown a small portion of a vehicle wheel 22 the circumference or tire surface 22A of which cooperates with the road surface 21, i.e. more particularly with the road surface profile being denoted 21A. Thus in actual practice the contact between the tire surface 22A and the surface profile 21A will exist only at local small surface portions denoted $a_r$ and so forth in FIG. 2A. It has been found that the sum of these small areas $a_r + a_{r+1} \ldots a_{r+n}$ constitutes a very important magnitude, i.e. the so called real contact area A, as indicated in FIG. 2A. This real contact area A contributes to a substantial degree to explaining the friction properties in the relationship rubber wheel-surface.

Among many other specific parameters or factors being related to the contact area or interface between wheel tire and road surface as illustrated in FIG. 2A, there is also the so called relaxation, which it is attempted to illustrate at the indication 22R in FIG. 2A. There is here the question of propagation of the impressed small rubber portion as a result of a peak in profile 21A, further into the wheel rubber. During dynamic conditions when the wheel is rolling on road surface 21, time constants associated with such relaxation will play a role. Such relaxation and other specific factors in this-context are described in the litterature. As regards in particular the real contact area mentioned above, reference can be made to Greenwood, G. A. and Williamson, G.B.P., "Contact of Nominally Flat Surfaces", Proceedings of R. Society of London, Vol. A295, pp. 300–319, 1966.

As regards relationships or properties being associated with the road surface 21 or the profile 21A alone, the so called STDslope has a substantial significance in the invention. Other parameters or descriptors that may be mentioned are the texture curvature and the peak density, which will not be discussed more closely here. The STDslope referred to however, is very important and is described in, inter alia, $$a_r(v, V_S) = \frac{D}{2-D} \cdot \frac{2\sigma\tau^2}{\pi G^{d-1}\eta} \cdot \left[ e^{-\frac{b\delta}{r} \cdot \frac{V_s}{V}} + \frac{b\delta}{r} \cdot \frac{C_s}{v} - 1 \right] \left[ \frac{L^{(1-D)} - l^{(1-D)}}{1+D} \right] \quad (3)$$

Longuept-Higgins, M. S., "Statistical Analysis of Random: moving surface", Philtrans.Royal Soc., vol A295 pp. 300–319, 1957.

The STDslope is the standard deviation of the road surface texture, i.e. the surface slopes, which is a usual measureable parameter by means of electronic texture measurement instruments. Previous utilization of the notion of or magnitude STPslope is as description of stochastic surfaces and is not employed in connection with wheel friction or visco elastic material such as rubber.

In the following discussion and the mathematical relations referred to, there are involved a series of parameters or magnitudes being hitherto used substantially with respect to the rubber material as such, but being here employed in an analogous meaning for a rubber wheel being constructed also with elements of other materials than rubber. For example, the tire or wheel viscosity can be defined in the same way as the viscosity of a material. The spring constant for the deformation of a rubber wheel gives a higher counter force at increasing deformation speed. This involves a certain difference between rubber .tires and rubber materials. However, an analogy is present.

If now FIG. 2B in particular is considered, there is illustrated a method for ,describing the surface roughness or variations in profile 21A. Between preferably evenly distributed points of profile 21A, there are drawn straight lines, of which two line pieces h1 and h2 are indicated specifically in FIG. 2B. These line pieces run at varying angles in relation to for example the horizontal, and represents a number of surface slopes h1, h2, . . . hN as indicated in FIG. 2B. The horizontal distance between the points indicated can for example-in practice be two millimeter. This manner of observation forms the basis of the parameter STPslope mentioned above, and from this as well as experiments performed, it is found that STDslope together with the real contact area $A_r$ to a substantial degree determines the before mentioned $\mu_{max}$ Generally according to the invention, it has been found that the following the relation applies:

$$\mu_{max} = -f + g \cdot STDslope - h \cdot A_r(v, V_s) \quad (2)$$

More particularly experiments as mentioned, with subsequent processing of experimental data by regression analysis, have resulted in the following figures for the constant f, g and in the above relation (2):

$f = 0{,}25$    preferably $f = 0{,}26$
$g = 0{,}015$
$h = 0{,}3$    preferably $h = 0{,}305$.

These numerical values, i.e. more particularly the indicated preferred figsures, are determined with a fit goodness of R=0,97. As regards methods within the field of regression analysis reference can be made to text books in mathematics, such as: Richard J. Larsen and Morris L- Marx, "An Introduction to Mathematical Statistics and Its Applications", Prentice-Hall, Englewood Cliffs, N.J.

An additional mathematical discipline being of interest in the present context, is the fractal-mathematics, as will appear from the following relation concerning the above mentioned $A_r$:

wherein
D=fractal dimension
G=fractal scaling factor
L=upper wave length cut-off limit for a chosen number of sinusoidal waves
L=lower wave length cut-off limit for a chosen number of sinusoidal waves
σ=stress-factor for the rubber wheel
τ=the rubber wheel relaxation spectra
η=the rubber wheel viscosity
δ=rubber wheel shape-factor
b=the length of the contact area between the wheel and the surface
r=the rubber wheel radius.

The upper and lower wave length limits respectively, as stated above, apply to sinus or cosinus curves of different wavelength and phase angles, which in super position can be used for describing surface profiles or areas having a roughness, such as illustrated in FIGS. 2A and 2B. The question of these wavelength limits in the present context, is connected to the fact that the texture roughness as for example represented by profile 21A in FIGS. 2A and 2B, in actual practice usually is within wavelength limits of 0,1 millimeter and 100 millimeter.

Regarding fractal methods, with reference to, inter alia, the magnitudes D and G above, reference can be made to Mandelbraut, B. B., "Self affined fractals and fractal dimensions", Physica Scripta Vol. 32, pp. 257–260, 1985.

The above relations (2) and (3) are incorporated in important features according to claim l, which in a relatively general form defines the method according to the invention for measuring or controlling friction relationships by interaction between rubber wheels and a surface during rolling movements under slip conditions. At this point, there is reason to consider FIG. 1 again, where there is drawn a so called maximum friction influence curve 8. This goes through the maximum points of the above mentioned curves 1, 2, 3 and 4. By means of the above mathematical relations, this maximum curve 8 is described and utilized, which to a high degree is characteristic to this invention. Thus in the various practical applications of the invention, i.e. both in measurements and in control functions, one will operate along this curve 8 in order to obtain optimum results.

Measurement methods based on the invention can be performed by means of an arrangement which in a simplified and purely schematic manner is illustrated in FIG. 3. This shows a surface or road 31 and a pneumatic rubber wheel 32 which can be caused to roll on surface 31. The wheel 32 is incorporated in measuring equipment and a measuring carriage or the like, comprising velocity censors 33 and 34 respectively for the rotation velocity of the wheel and for the linear velocity in relation to surface 31. The censor 34 for the latter velocity is not actually connected to the rotation of the schematically shown wheel axle 32A. From the rotational velocity and the radius of the wheel 32, seen in relation to the linear velocity v, the slip speed $V_s$ easily be calculated, possibly in a continuous manner during a test run. The calculation takes place in an electronic control unit for device 30, which also serves to control a traction manipulated variable or control device represented by the block 35, for controlling or adjusting the rotational velocity of the wheel in a desired manner during the measurement.

When in particular there is the question of measurements of properties of the vehicle wheel, relation (3) can be simplified to the following:

$$A_r(v, V_s) = K \left[ e^{-W\frac{V_s}{v}} + W\frac{V_s}{v} - 1 \right] \quad (4)$$

Where K=

$$\frac{D}{2-D} \quad \frac{2\sigma\tau^2}{nG^{(D-1)}\eta} \left[ \frac{L^{(1+D)} - l^{(1+D)}}{1+D} \right]$$

i.e. based upon known friction properties of the road surface 31, which can be for example a standard surface. When combining the above relation (4) with the previously mentioned relation (2), K can be expressed directly by eliminating $A_r$, so that we will find $$K = \frac{\mu_{max} + f - gSTD\text{slope}}{h} \left[ e^{-W\frac{V_s}{v}} + W\frac{V_s}{v} - 1 \right] \quad (6)$$

In other words K is a measure for the traction properties of the rubber wheel or tyre. Such measurements is preferably based on a horizontal surface 31, which is also preferred in cases where the measurement is directed to the friction properties of the surface itself. As an alternative, it is possible to take two measurements for determining both K and W.

As stated in claim 3 with respect to measurements of the traction properties of pneumatic rubber wheels, the maximum friction value $\mu_{max}$ is preferably measured simultaneously during the time interval of the actual run with the arrangement in FIG. 3, whereby the two parameters b and δ included in W in relation (6), are considered to be known or possibly measured before hand by means of measuring methods being known per se.

In the case of measuring friction properties of a surface based on the use of rubber wheel, the traction properties of which are known, relation (3) can be simplified to the following:

$$A_r(v, V_s) = \frac{D}{(2-D)G^{(D-1)}} HM \left[ \frac{L^{(1+D)} - l^{(1+D)}}{1+D} \right] \quad (5)$$

Here there is included a constant H $$H = \frac{2\sigma\tau^2}{\pi\eta}$$

whereby the constant is determined by the known properties of the rubber wheel. Moreover, in relation (5) there is included a magnitude M being of the form:

$$M = \left[ e^{-\frac{b\delta}{r} \frac{vt}{v}} + \frac{b\delta}{r} \frac{V_s}{v} - 1 \right]$$

As will appear from the expression above, M is in part determined by known properties of the rubber wheel and in part by the velocities v and $V_s$.

In relation (5) above there are magnitudes representing measurement values being sought for the friction properties of the surface, i.e. the magnitudes D and G. Since these represent to unknown values in this connection, the measurements of surface friction according to the invention is performed by two runs in a given time interval with a first linear vehicle velocity and a second vehicle velocity respectively, being different from the first velocity. If desired, it is of course possible to carry out more runs for arriving at more exact final results by suitable processing of the acquired measuring data. As already mentioned above with reference to FIG. 3, the slip speed $V_s$ is measured and controlled also during these measurements, so that this value is fully monitored for the determination of M.

In a simplified and schematic manner FIG. 4 shows a vehicle with four wheels 41, 42, 43 and 44 with equipments and means for controlling the traction conditions for the vehicle, which can be considered to be a regulating process for the purpose of either braking or accelerating the vehicle. A braking process usually will take place during a relatively short time interval, as mentioned above, whereby an optimal regulation of the braking power is very important. For the wheel 41, there are shown two velocity censors 48 and 49 respectively for the rotational velocity of the wheel and for the linear velocity of the vehicle in relation to the pavement. As previously described this makes possible a continuous calculation of slip velocity $V_s$ which possibly by suitable signal processing is applied to a control device 50 as a regulating parameter therein. Resulting regulation gives a signal as a traction manipulated variable, represented by block 45, which in turn can influence the braking power for the wheel 41. Quite in analogy or complementary a propulsion power during acceleration can be controlled on the same basis.

As stated in claim 5 with respect to traction control for a vehicle having pneumatic rubber wheels, this control takes place with the slip speed $V_s$ as a regulating parameter, according to the relation $$\mu_{max} = A_r(v, V_s) = K \left[ e^{-W\frac{V_s}{v}} + W\frac{V_s}{v} + 1 \right]$$

during the whole traction process, i.e. the time interval which has also been referred to above, whereby a maximum value of $\mu_{max}$ is maintained.

In practical applications for traction control (braking or acceleration) there can be programmed a measurement as a first step in a braking procedure, for determining the properties of the vehicle tyre and the road surface-tyre properties. The process parameters acquired thereby, are introduced into the mathematical model for maximum friction in the control program. Then the braking regulation can continue according to a control program utilizing the maximum function curve. This means that force measurement is not employed further in the traction process, until it may be determined to perform a new measurement of the process parameters. The control or regulation device provides for running changes of the manipulated variable on the basis of the values of the physical parameters for the wheel, and the slip speed as well as their variation, in such a direction that the instantaneous slip velocity is obtained, which is characteristic to the maximum friction according to the influence curve of maximum friction.

We claim:

1. Method for measuring or controlling friction relationships when a pneumatic rubber wheel and a surface interact during rolling motion under slip conditions between the wheel and the surface, comprising continuous measurement of the linear velocity v of the wheel axle in relation to the surface and continuous measurement of the rotational velocity of the wheel within an acceleration or deceleration time interval during the rolling motion of the wheel in relation to the surface, calculation of a corresponding, varying slip speed $V_s$ from said linear velocity v being measured and said rotational velocity being measured while taking the wheel radius into account, and calculation of friction relationships occuring during said time interval, characterized in that measurement values or control parameters relating to said friction relationships are calculated as a function of the varying slip speed $V_s$ and the linear velocity v on the basis of the following relation(s):

$$\mu_{max} = -f + g \cdot STDslope - h \cdot A_r \ (v, V_s)$$

where $\mu_{max}$ is the maximum friction value

STDslope is standard deviation of the surface texture slope angles, as measured for example with a known measurement method, $A(v,V_s)$ is the real or total contact area between the wheel and the surface, as a function of the velocities v and $V_s$ and $$A_r(v, V_s) = \frac{D}{2-D} \ \frac{2\sigma\tau^2}{\pi G^{d-1}\eta} \cdot \left[ e^{-\frac{b\delta}{r} \ \frac{V_s}{v}} + \frac{b\delta}{r} \ \frac{V_s}{v} - 1 \right] \left[ \frac{L^{(1-D)} - l^{(1+D)}}{1+D} \right]$$

where

D=fractal dimension

G=fractal scaling factor

L=upper wave length cut-off limit for a chosen number of sinusoidal waves

L=lower wave length cut-off limit for a chosen number of sinusoidal waves

σ=stress-factor for the rubber wheel

τ=the rubber wheel relaxation spectra

η=the rubber wheel viscosity

δ=rubber wheel shape-factor b=the length of the contact area between the wheel and the surface r=the rubber wheel radius and where f, g and h are constants.

2. Method according to claim 1, characterized in selecting the following approximate numerical values for said constants:

f=0,25 preferably f=0,26 g=0,015 h=0,3 preferably h=0,305.

3. Method according to claim 1 for measuring traction properties of pneumatic rubber wheels when interacting with a surface, the friction properties of which are known, characterized in that the maximum friction value $\mu_{max}$ is measured, during said time interval, and that a measurement value K for said traction properties is calculated on the basis of the relation $$K = \frac{\mu_{max} + f - g \cdot STDslope}{h} \ [e^{-W\frac{V_s}{v}} + W\frac{V_s}{v} - 1]^{-1}$$

where

STDslope is known for the surface concerned

W is equal to b·δ/r, b and δ being considered as known or possibly measured before-hand.

4. Method according to claim 3 wherein said surface is horizontal.

5. Method according to claim 1 for measuring friction properties of a surface, by interaction with a rubber wheel with known traction properties, characterized in that the maximum friction value $\mu_{max}$ and the corresponding critical slip speed $V_{max}$ are measured during said time interval at a first linear vehicle velocity, that the measurement of $\mu_{max}$ and $V_{max}$ is repeated at least once at a linear vehicle velocity being different from said first velocity, and that measurement values D and G for the friction properties are calculated on the basis of the relation $$A_r(v,V_s) = \frac{D}{(2-D)G^{(D-1)}} \ HM \left[ \frac{L^{(1+D)} - l^{(1+D)}}{1+D} \right]$$

where $$H = \frac{2\sigma\tau^2}{\pi\eta}$$

H being a constant determined by known properties of the rubber wheel, and $$M = \left[ e^{-\frac{b\delta}{r} \ \frac{V_s}{v}} + \frac{b\delta}{r} \ \frac{V_s}{v} - 1 \right]$$

M being determined in part by known properties of the rubber wheel and in part by the velocities v and Vs.

6. Method according to claim 5 wherein said surface is horizontal.

7. Method according to claim 1 for controlling a traction process (braking or propulsion) during a said time interval, for a vehicle with pneumatic rubber wheels, by means of a regulating device which under the effect of control parameters control a traction manipulated variable (braking or acceleration power) in order to obtain a predetermined friction relationships, and based upon known traction properties (K) of the vehicle wheels, characterized in that at least one control parameter is derived from the vehicle velocity, and the slip speed is adjusted continuously on the basis of the relation, $$\mu_{max} \cong A_r(v,V_s) = K \left[ e^{-W\frac{V_s}{v}} + W\frac{V_s}{v} + 1 \right]$$

so as to maintain a maximum value of $\mu_{max}$ during the whole of said time interval.

8. Method according to claim 7 wherein said at least one control parameter is continuously derived.

9. Apparatus for measuring or controlling friction relationships when a pneumatic rubber wheel and a surface interact during rolling movement under slip conditions between the wheel and the surface, comprising means for continuous measurement of the linear velocity v of the wheel axle in relation to the surface and continuous measurement of the rotational velocity of the wheel within an acceleration or deceleration time interval during the rolling motion of the wheel in relation to the surface, means for calculation of a corresponding, varying slip speed $V_s$ from said linear velocity v being measured and said rotational velocity being measured while taking the wheel radius into account, and means for calculation of friction relationships occuring during said time interval, characterized by means for calculating measurement values or control parameters depending on the varying slip speed $V_s$ and the linear velocity v on the basis of the following relations:

$$\mu_{max} = -f + g \cdot STDslope - h \cdot A_r(v, V_s)$$

where $\mu_{max}$ is the maximum friction value

STDslope is standard deviation of the surface texture slope angles, measured for example with a. known measuring method, $A_r(v, V_s)$ is the real or total contact area between the wheel and the surface, as a function of the velocities v and $V_s$, and $$A_r(v, V_s) = \frac{D}{2-D} \frac{2\sigma\tau^2}{\pi G^{d-1} \eta} \left[ e^{-\frac{b\delta}{r} \frac{V_s}{v}} + \frac{b\delta}{r} \frac{V_s}{v} - 1 \right] \left[ \frac{L^{(1-D)} - l^{(1+D)}}{1+D} \right]$$

where
wherein

D=fractal dimension
G=fractal scaling factor
L=upper wave length cut-off limit for a chosen number of sinusoidal waves
L=lower wave length cut-off limit for a chosen number of sinusoidal waves
σ=stress-factor for the rubber wheel
τ=the rubber wheel relaxation spectra
η=the rubber wheel viscosity
δ=rubber wheel shape-factor
b=the length of the contact area between the wheel and the surface
r=the rubber wheel radius,
and where f, g and h are constants.

10. Apparatus according to claim 9 for measuring traction properties of pneumatic rubber wheels when interacting with a surface with known friction properties, characterized by means for measuring the maximum friction value $\mu_{max}$, during said time interval, and means for calculating a measurement value K for the traction properties on the basis of the relation:

$$K = \frac{\mu_{max} + f - gSTDslope}{h} \left[ e^{-W\frac{V_s}{v}} + W\frac{V_s}{v} - 1 \right]$$

where

STDslope is known for the surface concerned

W is equal to b·δ/r.

11. Apparatus according to claim 10 wherein said surface is horizontal.

12. Apparatus according to claim 9 for measuring friction properties of a surface, by interaction with a rubber wheel with known traction properties, characterized by means for measuring the maximum friction value $\mu_{max}$ and a corresponding critical slip speed $V_{max}$, during said time interval at a first linear vehicle velocity, whereby the measurement of $\mu_{max}$ and $V_{max}$ is repeated at least once at a linear vehicle velocity being different from said first velocity, and means for calculating measurement values D and G for the friction properties on the basis of the relation $$A_r(v, V_s) = \frac{D}{(2-D)G^{(D-1)}} HM \left[ \frac{L^{(1+D)} - l^{(1+D)}}{1+D} \right]$$

where $$H = \frac{2\sigma\tau^2}{\pi\eta}$$

H being a constant determined by known properties of the rubber wheel and $$M = \left[ e^{-\frac{b\delta}{r} \frac{V_s}{v}} + \frac{b\delta}{r} \frac{V_s}{v} - 1 \right]$$

M being determined in part by known properties of the rubber wheel and in part by the velocities v and Vs.

13. Apparatus according to claim 12 wherein said surface is horizontal.

14. Apparatus according to claim 9 for controlling a traction process (braking or a propulsion) during said time interval, for a vehicle with pneumatic rubber wheels, comprising a regulating device (50) which under the influence of control parameters control a traction manipulated variable (braking or acceleration power) for obtaining a predetermined friction relationships, and based upon known traction properties (K) of the vehicle wheels, characterized by means for deriving at least one control parameter from the vehicle velocity V, and means for continuously adjusting $V_s$ on the basis of the relation $$\mu_{max} \cong A_r(v, V_s) K \left[ e^{-W\frac{V_s}{v}} + W\frac{V_s}{v} - 1 \right]$$

so as to maintain a maximum value of $\mu_{max}$ during the whole of said interval.

15. Apparatus according to claim 14 wherein said at least one control parameter is continuously derived.

* * * * *

UNITED STATES PATENT AND TRADEMARK OFFICE
CERTIFICATE OF CORRECTION

PATENT NO. : 5,814,718
DATED : September 29, 1998
INVENTOR(S) : Arild Andresen et al.

It is certified that error appears in the above-indentified patent and that said Letters Patent is hereby corrected as shown below:

Col. 4, line 45, "A," should be -- $A_r$ --; Col. 4, line 46, "A" should be -- $A_r$ --; Col. 5, line 3 (equation 3), "a" should be -- A --; Col. 6, line 15, "L" should be -- $\ell$ --; In the Claims: Col. 9, line 42 (claim 1), "L" should be -- $\ell$ --; Col. 11, line 42 (claim 9), "L" should be -- $\ell$ --.

Signed and Sealed this

Twenty-seventh Day of July, 1999

Attest:

Q. TODD DICKINSON

*Attesting Officer*          *Acting Commissioner of Patents and Trademarks*